(12) United States Patent
Shao

(10) Patent No.: US 12,251,330 B2
(45) Date of Patent: Mar. 18, 2025

(54) HYDROTHERAPY CUP

(71) Applicant: Shenzhen Hijoy Technology Co., Ltd., Shenzhen (CN)

(72) Inventor: Zhubiao Shao, Shenzhen (CN)

( * ) Notice: Subject to any disclaimer, the term of this patent is extended or adjusted under 35 U.S.C. 154(b) by 0 days.

(21) Appl. No.: 18/799,971

(22) Filed: Aug. 9, 2024

(65) Prior Publication Data

US 2024/0398605 A1 Dec. 5, 2024

(51) Int. Cl.
*A61H 19/00* (2006.01)
*A61F 5/41* (2006.01)

(52) U.S. Cl.
CPC .............. *A61F 5/41* (2013.01); *A61H 19/00* (2013.01); *A61F 2005/412* (2013.01)

(58) Field of Classification Search
CPC ........ A61H 19/00; A61H 19/32; A61H 19/30; A61H 19/50; A61F 5/41; A61F 2005/411; A61F 2005/412; A61F 2005/414; A61F 2005/415
See application file for complete search history.

(56) References Cited

U.S. PATENT DOCUMENTS

| | | | | |
|---|---|---|---|---|
| 6,179,774 | B1 * | 1/2001 | Landry | A61H 33/60 600/38 |
| 11,998,501 | B2 * | 6/2024 | Truckai | A61H 9/0057 |
| 2012/0215142 | A1 * | 8/2012 | Spector | A61B 17/2251 601/46 |
| 2021/0369552 | A1 * | 12/2021 | Truckai | A61H 23/008 |
| 2024/0342051 | A1 * | 10/2024 | Truckai | A61H 23/008 |

* cited by examiner

*Primary Examiner* — Christine H Matthews
(74) *Attorney, Agent, or Firm* — Daniel M. Cohn; Howard M. Cohn

(57) ABSTRACT

A hydrotherapy cup includes a hydrotherapy cup shell; a fixed cover disposed on a top of the hydrotherapy cup shell; a power compartment disposed in the fixed cover and including an intake pipe, an exhaust pipe, a water pump connected to the exhaust pipe, and a battery pack electrically connected to the water pump; a control panel disposed on the fixed cover and electrically connected to the battery pack; a connecting pipe extending outward from a lower portion of the hydrotherapy cup shell; and a control element including a hose connected to the connecting pipe and a limiting valve disposed on the hose. The water pump may move fluids through the exhaust pipe to create a negative pressure in both the hydrotherapy cup shell and the power compartment.

1 Claim, 3 Drawing Sheets

HYDROTHERAPY CUP

TECHNICAL FIELD

The invention relates to the technical field of hydrotherapy cups, in particular to a hydrotherapy cup.

BACKGROUND ART

After the traditional physiotherapeutic instrument is sleeved, the silicone material below will stick close to the human organ, so that a sealing state is formed between the silicone material and the human organ. When the instrument operates, the instrument extracts air inside the silicone material, so that a negative pressure state is formed inside the silicone material, and the negative pressure can be controlled by adjusting the air pumping rate. Negative pressure environment can help the body organ recover. However, the physiotherapeutic instrument has a single experience feeling, and the negative pressure state is not conducive to the activity of the human organ, resulting in insufficient stimulation of the human organ and causing the human organ to be fatigued again.

Summary of the Invention

The invention aims to provide a hydrotherapy cup to solve the problems raised in the background art.

In order to realize the above purposes, the invention provides the following technical proposal: a hydrotherapy cup comprises a hydrotherapy cup shell, wherein a contact colloid is clamped at the bottom of the hydrotherapy cup shell, a power compartment is arranged at the upper end of the hydrotherapy cup shell, the hydrotherapy cup shell, the power compartment and the contact colloid form a cavity with holes at the bottom end, the holes are used for air and water circulation, bubbles are generated by the air circulation in the water and then have a massage effect, the power compartment comprises an intake pipe and an exhaust pipe connected with the cavity, a fixed cover is clamped at the upper end of the hydrotherapy cup shell, the power compartment is located in the fixed cover, a sealing ring is arranged at the connection of the power compartment and the fixed cover, a control panel is inlaid in the middle of the fixed cover, and a sealing ring is arranged at the connection of the power compartment and the hydrotherapy cup shell.

Preferably, the contact colloid is a silicone which is an elastic structure.

Preferably, an integrally formed connecting pipe is arranged on the bottom side wall of the hydrotherapy cup shell and is externally connected with a control element to control the flow rate, and water or air enters the cavity through the connecting pipe when the interior of the cavity is in a negative pressure state.

Preferably, the negative pressure in the cavity is realized by the power compartment located at the top, a water pump and a battery pack are arranged in the power compartment, the control panel is electrically connected with the water pump and the battery pack, the water pump is connected with the exhaust pipe, the water pump pumps out through the exhaust pipe to achieve a negative pressure state.

Preferably, the control element comprises a hose connected with the connecting pipe, a limiting valve is arranged in the middle of the hose, and the hose is a plastic, silicone or rubber pipe.

Preferably, the limiting valve is composed of a clamping frame and an extrusion wheel, wherein the clamping frame is sleeved onto the hose, a guide groove is arranged in the middle of the clamping frame and is inclined, the extrusion wheel is located in the guide groove, and the lower end of the extrusion wheel is propped against the hose.

Preferably, the limiting valve is a knob type valve.

Compared with the prior art, the invention has the following advantages: water is injected into the cavity through the connecting pipe, and then air is injected into the cavity through the connecting pipe to form bubbles, which can drive water inside the cavity to flow and then massage and bathe the human organ, making the users more comfortable and experience different feelings; the massage strength can be changed by changing the speed of air injection to adapt to the habits of different people.

Figure 1:
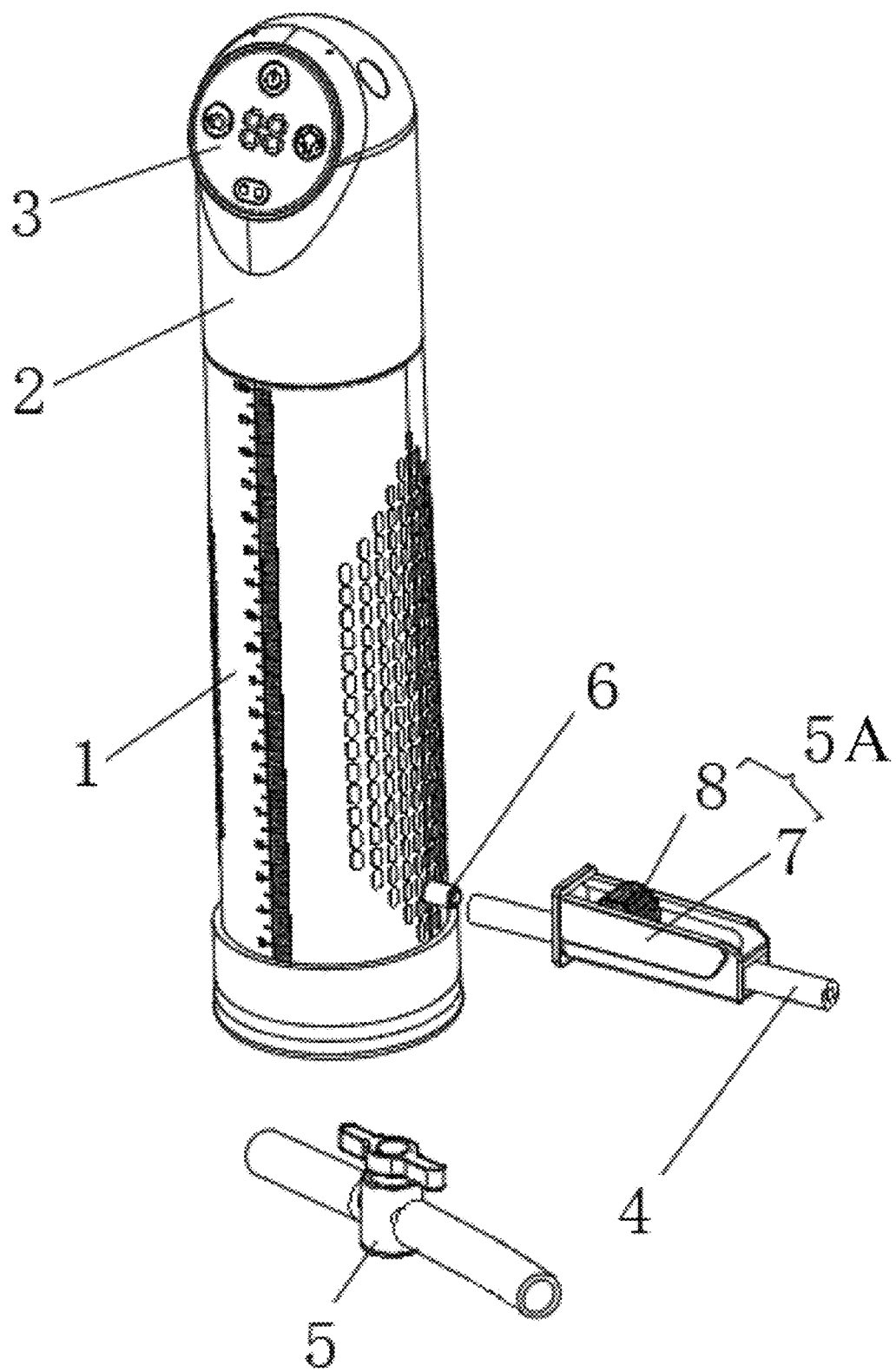
FIG. 1 is the connection diagram for the hydrotherapy cup body and the hose.

Reference characters in the drawings: 1. Hydrotherapy cup shell, 2. Fixed cover, 3. Control panel, 4. Hose, 5A. Limiting valve, 6. Connecting pipe, 7. Clamping frame, 8. Extrusion wheel, 9. Power compartment, 10. Intake pipe, 11. Exhaust pipe, 12. Battery pack, 13. Water pump.

DETAILED DESCRIPTION OF THE UTILITY MODEL INVENTION

In order to deepen the understanding and knowledge of the invention, the technical proposal in the embodiments of the invention will be clearly and completely described and introduced below in combination with the drawings to the embodiments of the invention. Obviously, the embodiments are only part of the embodiments of the invention, but not all the embodiments, not for restricting the embodiment in any form. Based on the embodiments of the invention, all other embodiments obtained by ordinary technicians in the field without making creative labor falls within the scope of protection of the invention.

Figure 2:
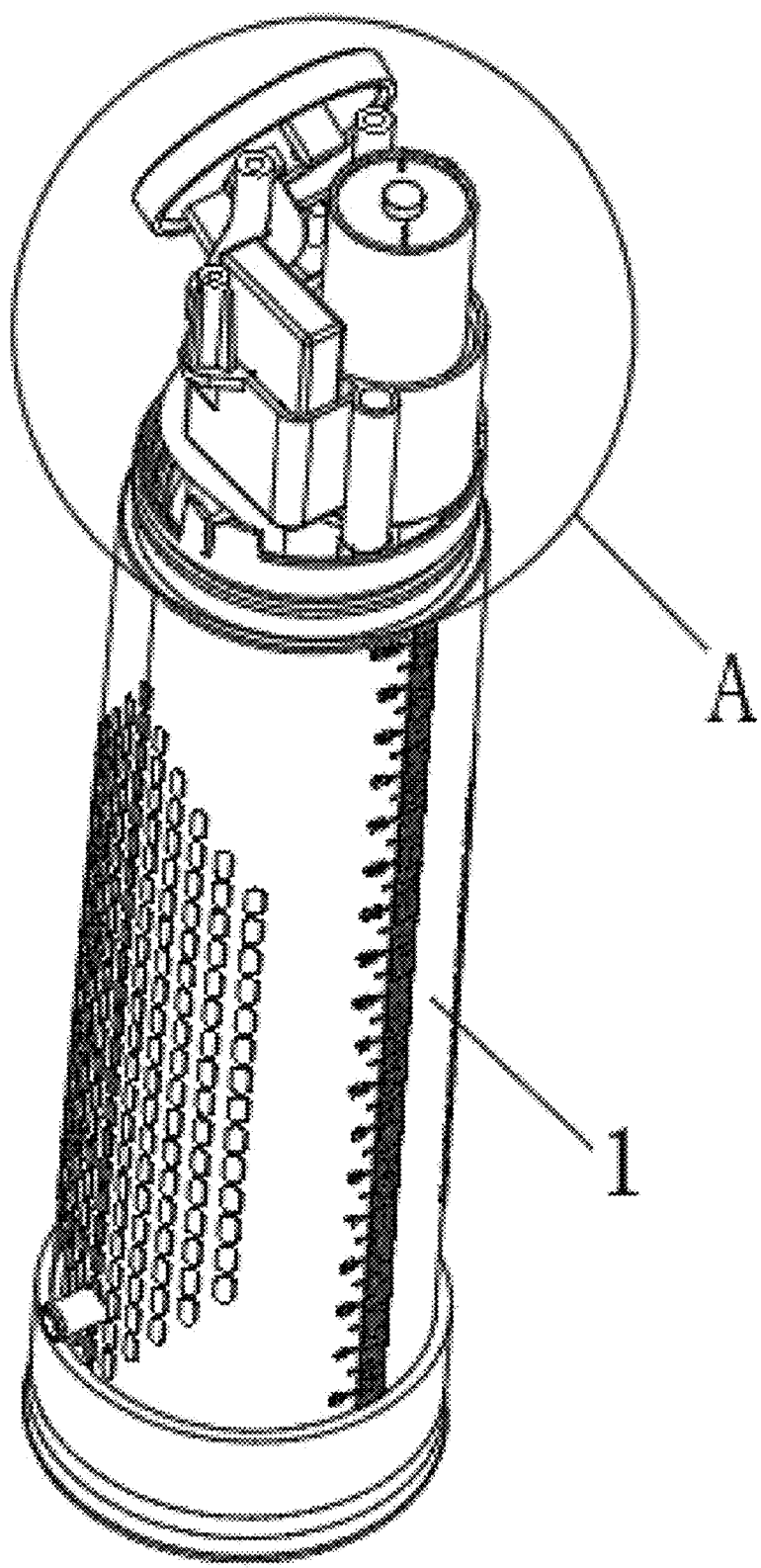
FIG. 2 is the internal connection diagram for the power compartment.
Figure 3:
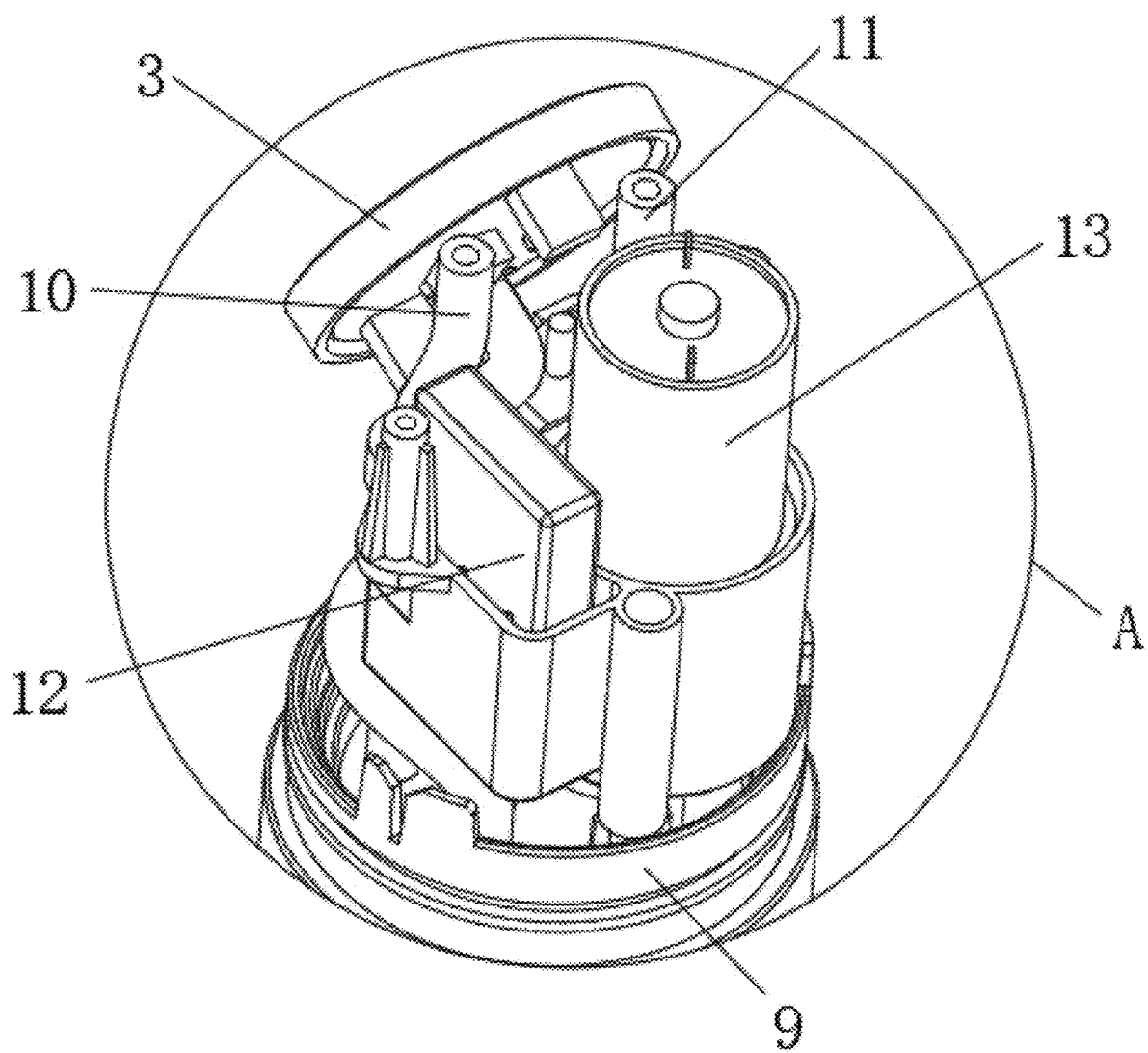
FIG. 3 is the enlarged view of the point A.

As shown in FIG. 1 to FIG. 3, the invention provides a technical proposal: a hydrotherapy cup comprises a hydrotherapy cup shell 1, a contact colloid is clamped at the bottom of the hydrotherapy cup shell 1, a power compartment 9 is arranged at the upper end of the hydrotherapy cup shell 1, the hydrotherapy cup shell 1, the power compartment 9 and the contact colloid form a cavity with holes at the bottom end, the holes are used for air and water circulation, and bubbles are generated by the air circulation in the water and then have a massage effect; the power compartment 9 comprises an intake pipe 10 and an exhaust pipe 11 connected with the cavity, a fixed cover 2 is clamped at the upper end of the hydrotherapy cup shell 1, the power compartment 9 is located in the fixed cover 2, and a sealing ring is arranged at the connection of the power compartment 9 and the fixed cover 2 to prevent water from entering the power compartment 9, resulting in damage to electronic devices; a control panel 3 is inlaid in the middle of the fixed cover 2, and a sealing ring is arranged at the connection of the power compartment 9 and the hydrotherapy cup shell 1 to improve the sealing between the power compartment 9 and the hydrotherapy cup shell 1, preventing air or water leakage caused by gaps; the water pump 13 in the power compartment 9 is controlled through the control panel 3 to inject water and air into the internal cavity.

The contact colloid is a silicone which is an elastic structure; when being inserted into the human organ, the contact colloid can be deformed to be in contact with the human organ, and a sealing state is formed at the connection.

An integrally formed connecting pipe 6 is arranged on the bottom side wall of the hydrotherapy cup shell 1 and is externally connected with a control element 5 to control the flow rate, and water or air enters the cavity through the connecting pipe 6 when the interior of the cavity is in a negative pressure state; the negative pressure in the cavity is realized by the power compartment 9 located at the top, a water pump 13 and a battery pack 12 are arranged in the power compartment 9, the control panel 3 is electrically connected with the water pump 13 and the battery pack 12, the water pump 13 is connected with the exhaust pipe 11, and the water pump 13 pumps out through the exhaust pipe 11 to achieve a negative pressure state; the control element 5 comprises a hose 4 connected with the connecting pipe 6, a limiting valve 5A is arranged in the middle of the hose 4, and the hose 4 is a plastic, silicone or rubber pipe; when the hydrotherapy cup is used, the hose 4 can be inserted into the water first, and the water pump 13 can pump out the air inside the cavity, thus forming a negative pressure state, which can help the human organ erect, and the cavity can suck water under the negative pressure state, thus filling the cavity with water; then the excess water can be discharged from the exhaust pipe 11; after the cavity is filled with water, the hose 4 is drawn from the water; at this time the water pump can inject air into the cavity through the hose 4, and then bubbles can be formed in the cavity, which can drive the water inside the cavity to flow and then massage and bathe the human organ, thus achieving a more comfortable medicated bath effect.

The limiting valve 5A is composed of a clamping frame 7 and an extrusion wheel 8, wherein the clamping frame 7 is sleeved onto the hose 4, a guide groove is arranged in the middle of the clamping frame 7) and is inclined, the extrusion wheel 8 is located in the guide groove, and the lower end of the extrusion wheel 8 is propped against the hose 4; the limiting valve 5A is a conventional knob type valve; the speed of water and air flow into the cavity is controlled by controlling the limiting valve 5A, thus giving the user a different experience.

Embodiment 1: The hydrotherapy cup of the invention can be used as a traditional erection device. Before the operation of the equipment, the hose 4 is squeezed and sealed through the limiting valve 5A. After the operation of the equipment, the water pump pumps out air in the internal cavity through the exhaust pipe, thus forming a negative pressure state in the internal cavity, promoting the erection of the human organ and changing the feeling of the human organ by changing the negative pressure;

Embodiment 2: On the basis of Embodiment 1, the limiting valve 5A is opened, and water is first injected into the internal cavity through the connecting pipe 6 until the internal cavity is filled with water. If water is continued to be sucked at this time, the water will be discharged from the exhaust pipe. When the internal cavity is filled with water, the gas is injected into the internal cavity through the hose, and then bubbles are formed to drive the water inside the cavity to flow and then massage and bathe the human organ, thus achieving a more comfortable medicated bath effect.

Although the embodiments of the invention have been shown and described, it should be emphasized that the above description is only an introduction and description for the mode of use of the embodiments of the invention, and is not a restriction on the invention in any form. For ordinary technicians in the field, it can be understood that these embodiments may be changed, modified, substituted and varied without deviation from the principle and spirit of the invention, and the scope of the invention is limited by the claims and their equivalents.

The invention claimed is:

1. A hydrotherapy cup, comprising:
   a hydrotherapy cup shell;
   a fixed cover disposed on a top of the hydrotherapy cup shell;
   a power compartment disposed in the fixed cover and comprising an intake pipe, an exhaust pipe, a water pump connected to the exhaust pipe, and a battery pack electrically connected to the water pump;
   a control panel disposed on the fixed cover and electrically connected to the battery pack;
   a connecting pipe extending outward from a lower portion of the hydrotherapy cup shell; and
   a control element comprising a hose connected to the connecting pipe and a limiting valve disposed on the hose;
   wherein the water pump is configured to move fluids through the exhaust pipe to create a negative pressure in both the hydrotherapy cup shell and the power compartment; and
   wherein the limiting valve comprises a clamping frame disposed on the hose and an extrusion wheel urging against the hose.

\* \* \* \* \*